(12) United States Patent
Sieracki

(10) Patent No.: US 7,575,594 B2
(45) Date of Patent: Aug. 18, 2009

(54) SHOCK DAMPENING BIOCOMPATIBLE VALVE

(76) Inventor: Jeffrey M. Sieracki, 13506 Collingwood Ter., Silver Spring, MD (US) 20904

( * ) Notice: Subject to any disclaimer, the term of this patent is extended or adjusted under 35 U.S.C. 154(b) by 148 days.

(21) Appl. No.: 11/320,819

(22) Filed: Dec. 30, 2005

(65) Prior Publication Data

US 2006/0149367 A1  Jul. 6, 2006

Related U.S. Application Data

(60) Provisional application No. 60/640,499, filed on Dec. 30, 2004.

(51) Int. Cl.
*A61F 2/24* (2006.01)
(52) U.S. Cl. ............................ 623/2.2; 623/2.34
(58) Field of Classification Search ............. 623/1.24, 623/1.26, 2.2–2.34; A61F 2/24
See application file for complete search history.

(56) References Cited

U.S. PATENT DOCUMENTS

| | | | |
|---|---|---|---|
| 4,692,164 A * | 9/1987 | Dzemeshkevich et al. .. | 623/2.14 |
| 4,888,010 A | 12/1989 | Bokros | |
| 5,116,367 A | 5/1992 | Hwang et al. | |
| 5,314,467 A * | 5/1994 | Shu ........................... | 623/2.28 |
| 5,354,330 A | 10/1994 | Hanson et al. | |
| 5,405,381 A | 4/1995 | Olin | |
| 5,449,384 A * | 9/1995 | Johnson ...................... | 623/2.14 |
| 5,607,470 A | 3/1997 | Milo | |
| 5,628,791 A | 5/1997 | Bokros et al. | |
| 5,772,694 A | 6/1998 | Bokros et al. | |
| 5,824,062 A | 10/1998 | Patke et al. | |
| 5,957,949 A * | 9/1999 | Leonhardt et al. .......... | 623/1.24 |
| 6,039,759 A * | 3/2000 | Carpentier et al. ............ | 623/2.2 |
| 6,206,918 B1 | 3/2001 | Campbell et al. | |
| 6,371,983 B1 * | 4/2002 | Lane .......................... | 623/2.14 |
| 6,395,024 B1 | 5/2002 | Lapeyre et al. | |
| 6,461,382 B1 | 10/2002 | Cao | |
| 6,589,279 B1 * | 7/2003 | Anderson et al. .......... | 623/2.13 |
| 6,645,244 B2 | 11/2003 | Shu et al. | |
| 6,770,062 B2 * | 8/2004 | Phung et al. ................. | 604/320 |
| 6,821,297 B2 * | 11/2004 | Snyders ..................... | 623/2.18 |
| 7,238,200 B2 * | 7/2007 | Lee et al. .................... | 623/2.14 |
| 2003/0069635 A1 | 4/2003 | Cartledge et al. | |
| 2005/0049698 A1 | 3/2005 | Bolling et al. | |
| 2005/0060029 A1 | 3/2005 | Le et al. | |
| 2005/0096739 A1 | 5/2005 | Cao | |

* cited by examiner

*Primary Examiner*—Corrine M McDermott
*Assistant Examiner*—Jason-Dennis Stewart
(74) *Attorney, Agent, or Firm*—Rosenberg, Klein & Lee

(57) ABSTRACT

A biocompatible valve (200) includes a valve mechanism (250, 230*a*, 230*b*), which is mounted and is longitudinally displaceable within a valve mount (210) affixed to a recipient patient. A valve annulus (250) defines an orifice (240) in which a closing mechanism (230*a*, 230*b*) is received. Upon a transition from an open position to a closed position of the closing mechanism (230*a*, 230*b*), hydraulic shock is introduced into the fluid passing through the valve. The present invention provides a dampening mechanism (280) to mitigate the shock and to dissipate its energy. Various embodiments allow for high order frequency response through relationships between dampening mechanism components.

28 Claims, 9 Drawing Sheets

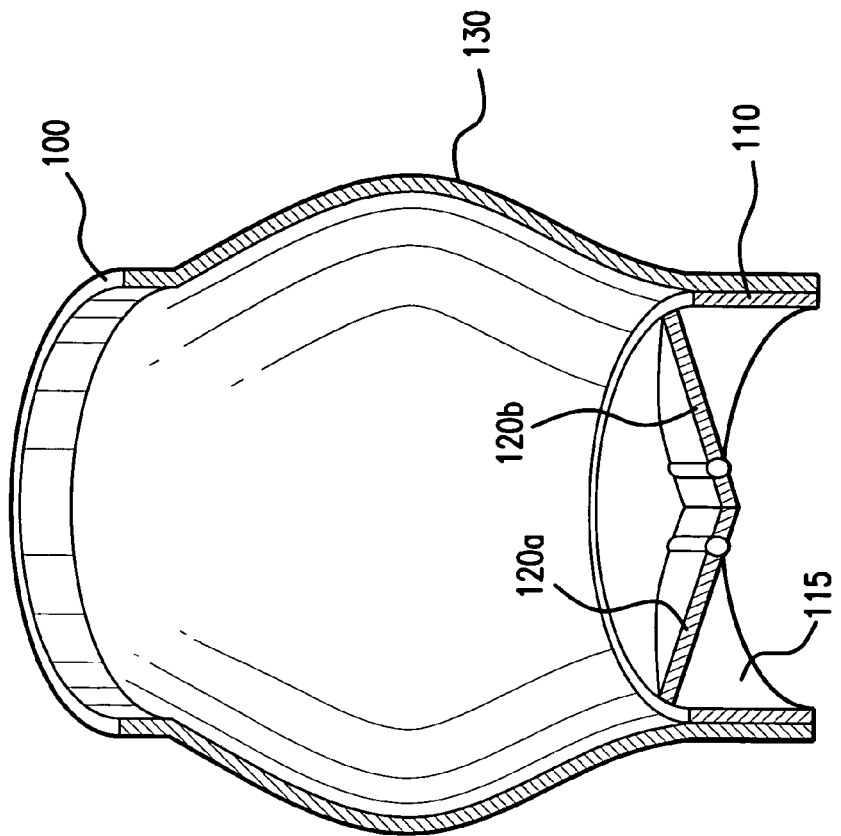
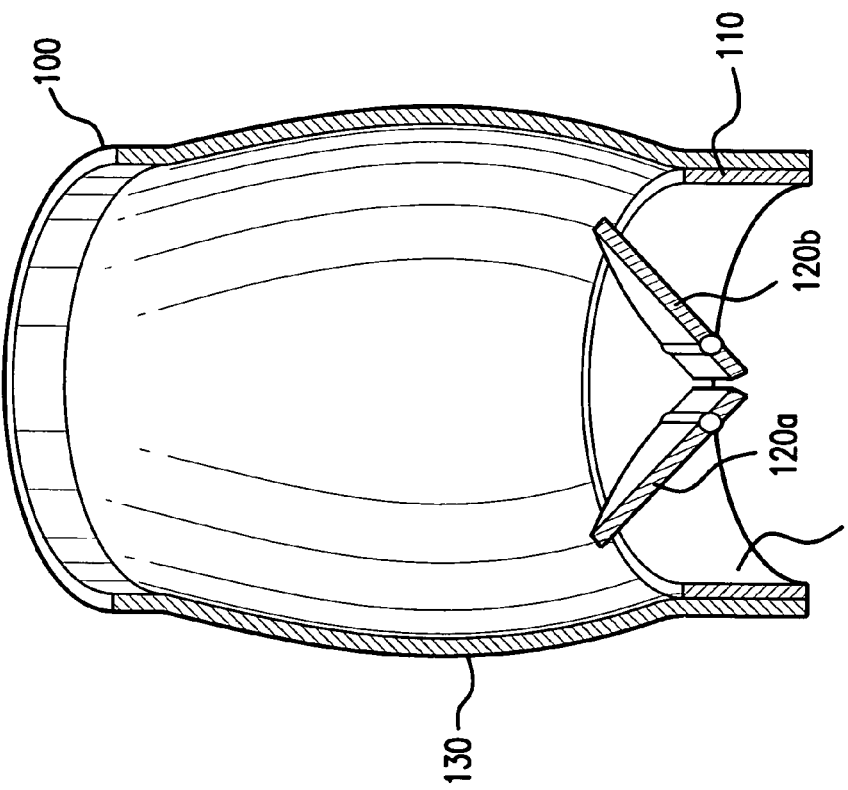
PRIOR ART
FIG. 1A
PRIOR ART
FIG. 1B

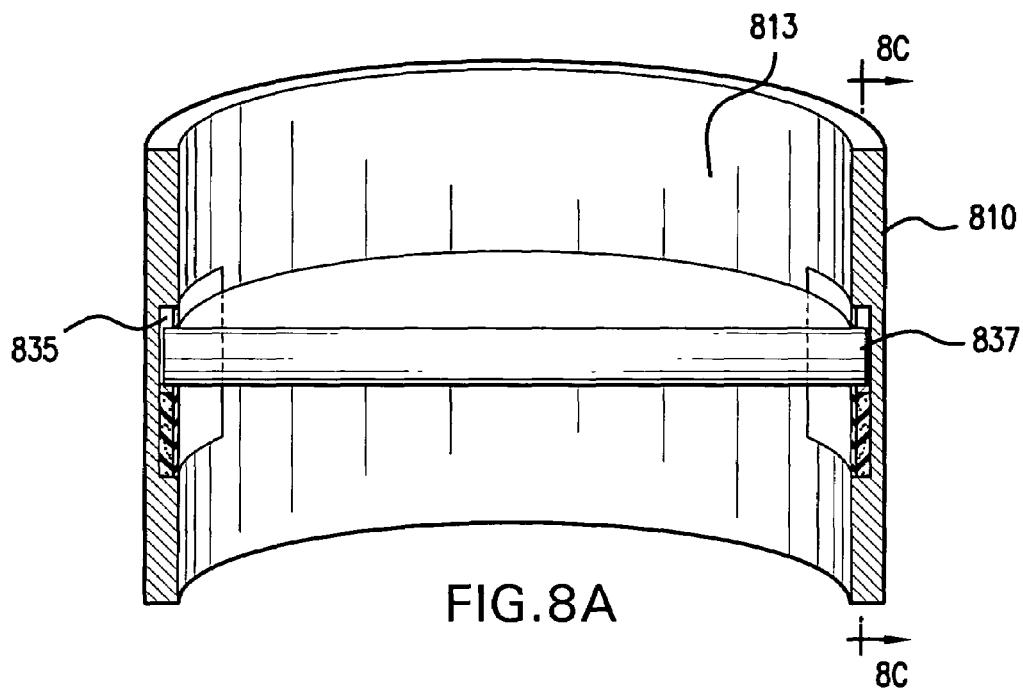
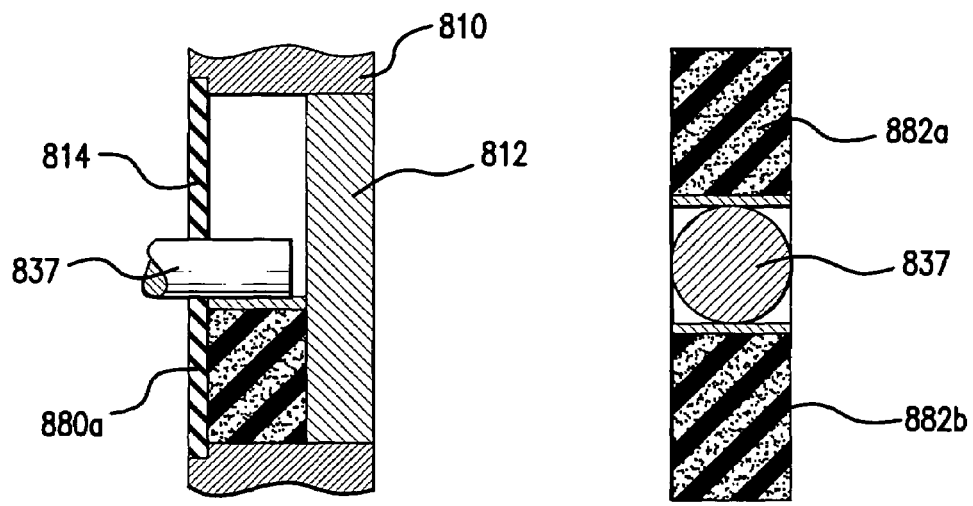

SHOCK DAMPENING BIOCOMPATIBLE VALVE

RELATED APPLICATION DATA

This Patent Application is based on a Provisional Patent Application Ser. No. 60/640,499, filed on 30 Dec. 2004.

BACKGROUND OF THE INVENTION

1. Field of the Invention

The invention described herein is directed to prosthetic valves, such as mechanical heart valves adapted for surgical implantation to a patient. More specifically, the invention is operable to mitigate audible noise, physical discomfort, and mechanical stress on both the replacement valve and patient tissues that is caused from hydraulic shock in the fluid when the valve through which the fluid flows undergoes a transition from an open position to a closed position.

2. Brief Description of the Prior Art

The surgical replacement of natural heart valves with durable, artificial valves in living patients has become commonplace due to the reliability of such valves achieved in the past several decades. Among the prosthetic replacement valve options are "tissue valves", which are valves taken from deceased donors or even animals, and "mechanical valves", which replace the soft tissue valves with those of various biocompatible manufacturing materials. Both of these options suffer from various problems and deficiencies.

Mechanical valves, due to the presence of fixed hard edges and other biological incompatibility factors, are prone to the formation of potentially damaging blood clots in the recipient patient. Thus, anti-coagulation therapy is generally required as an adjunct to mechanical valve implants. Tissue valves do not require such anti-coagulation treatment, but tend to stiffen and calcify over a relatively short lifetime (such as after ten years) and then require replacement. Despite the requirement of sustained medical treatment with anti-coagulation drugs, mechanical valves are often preferable over tissue valves in patients expected to live postoperatively longer than ten or fifteen years, because implanting a prosthetic valve may reduce the likelihood of additional surgery to replace the valve.

Considerable design effort has been directed towards moderating the drawbacks of mechanical prosthetic valves. Of these drawbacks, mechanical valve noise has been brought forward as a prominent complaint by many mechanical valve recipients. Tissue valves are quiet due to certain natural properties inherent to their leaflet and substrate elasticity and because of their quasi-optimal evolutionary shape. Mechanical valves by contrast, due to limitations of manufacturing processes and materials, can be quite noisy. Noise problems are compounded in the presence of a graft, such as an aortic root replacement, that removes the acoustic and shock absorptive properties normally afforded by the surrounding natural tissue structures. Unfortunately, it is common for both the ascending aorta and aortic valve to be replaced simultaneously in the same operation, such as for patients with an aortic aneurysm.

A typical contemporary artificial heart valve includes a fixed annulus in which are suspended one or more gating flaps or "leaflets". This design has replaced early ball-and-cage designs, which have since been outmoded. The leaflets are hinged so as to open by blood flow during systole and to close and seal against the surrounding orifice during diastole, when blood flow begins to reverse. Generally, mechanical valves are composed of metals, carbon composites, pyrolytic carbon, or various hybrid combinations that are fairly stiff and durable, but the closing of these valves introduces noise that is both heard and felt by mechanical valve recipient patients.

There are two distinct components to the noise generated by the valve when it is closed. A first component arises from the impact of the leaflets against the orifice. In patients that have received a mechanical valve, this is typically experienced as an audible "click" or metallic "tink" sound occurring at each heartbeat. Since these valves close under considerable pressure, the impact forces can be substantial and the resulting sound may be quite loud.

A second component of valve noise arises from the phenomena of hydraulic shock. Whenever a fluid flow is suddenly interrupted, it creates a shock wave that propagates back through the system by way of the fluid medium and resonates until it is damped by the natural properties of the system. The force of this shock can be quite strong. In plumbing, a similar phenomenon is referred to as "water hammer" and the forces generated are known by plumbers to be potentially damaging in magnitude.

The noise components of mechanical heart valves are well documented by patient recipients thereof. These patients, and even their families, complain of a ticking or similarly unnatural sound emanating from the patient and over time, adapt to accommodate them. The ticking sound of a valve leaflet closing is clearly audible to third parties, definitely mechanical in tone, and present in nearly all patients, regardless of body fat or other factors.

The noise attributed to hydraulic shock is not clearly audible to an external party without deliberate observation, such as through a stethoscope or by close contact. This noise component has a much duller and "natural" tone and its amplitude varies depending upon the recipient's breathing, body position, and body fat. Previously, the focus of physicians and other specialists has been on addressing the most obvious issues first. Thus, there are numerous devices that concern themselves with moderating the ticking heart valve noise of the valve leaflet striking the sides of the orifice. Such designs of the prior art have generally focused on slowing or modifying the final closing stages of the leaflets so as to lessen the impact noise. The second, shock component of the noise, however, has been largely ignored by heart valve designers.

Nonetheless, shock noise is a persistent complaint in patients. Due to sound conduction through tissue and bone, the shock noise is much more audible to the patient than to an external party. Additionally, the hydraulic shock is sometimes extremely strong and has very low frequency components that may present an uncomfortable physical "thumping" sensation in the chest wall.

Psychoacoustic stress notwithstanding, the hydraulic shock involved in these mechanical replacement valves present physical forces that may very well shorten the life of the valve and may cumulatively damage major blood vessels or other body tissue. The hydraulic shock is a particular problem in aortic valve replacements in that the aortic valve is situated between the final pumping chamber of the heart and the aorta. The blood is pushed through the aortic valve to the entire body and thus, the pressures are highest and the shock greatest at that point.

In the natural cardiovascular system, soft tissue in arterial walls in certain cavity structures known as "sinuses" act to absorb and dampen hydraulic shock. The mechanical valve, however, generates a much more abrupt interruption of flow than a tissue valve due to the stiffness of the components composing the valve. Natural structures may be inadequate for absorbing the shock. Furthermore, when a synthetic arterial graft is introduced with the mechanical valve, as is common in aortic aneurysm repair, the combined system loses many of the natural dampening features and the problem is significantly worsened.

Referring now to FIGS. 1A and 1B, there is shown a valve and graft combination of the prior art having artificial sinuses incorporated in section of a graft downstream of the aortic valve. The prosthetic graft section 100 is adapted with the flexible elastic wall 130 that expands under high pressure and contracts with lower pressure. In FIG. 1A, the systolic stage of the heart beat cycle pushes blood through the valve 110 and thereby causing leaflets 120a, 120b to open by the force of the blood flow. At the outset of this stage, the elastic walls 130 are in a relatively contracted state and begin to stretch as they are filled with high-pressure blood from the heart. During the diastolic stage of the heart beat cycle, as shown in FIG. 1B, the blood flow begins to reverse at the valve and thereby forces the leaflets to close against the orifice 115. The pressure shock wave introduced to the fluid by the closing of the valve is transmitted in part to the elastic walls 130, which then expand an additional amount to absorb the shock energy. The effect of the device is two-fold. First, it dampens the pulses of each heart beat to a more sustained flow, as would the flexible walls of a natural aorta. Secondly, the elasticity dampens shock waves that would otherwise resonate through the system had a stiff tube been implemented for the artificial aorta.

The design illustrated in FIGS. 1A-1B is not optimized to effectively dampen hydraulic shock. The elastic section 130 stretches under pressure during the ejection of blood from the heart. Then, as the blood flow reverses, the elastic section 130 contracts and contributes to a force that causes the leaflets 120a, 120b to close against the orifice 115 slightly harder and faster than would occur had the elastic walls not been introduced. Furthermore, the shockwave caused by the mechanical transition of state of the valve will be only partially damped by the elastic walls. Additional shockwaves reflected through the system and back to the valve will also be only partially damped by the semi-relaxed sinus walls, i.e., the sinuses will not be fully relaxed when the shockwave arrives. Thus, dampening will not be optimal. Moreover, the elastic expansion occurs perpendicular to blood flow, i.e., in a radial direction, and is therefore not well suited to absorbing shock energy from a compression wave moving longitudinally through the system.

An additional problem arises with artificial sinuses in that they are susceptible to scarring. It is common in aortic grafts that accumulation of a centimeter or more of fibrous scar tissue forms as the body reacts to the presence of the artificial material. This fibrous tissue is much less flexible than the natural arterial walls and less flexible than the artificial sinus cavity walls. Over time, the scar tissue will tend to stiffen the elastic walls, which then precludes expansion and contraction. Should the walls stiffen to a point where they are maintained in a position that causes blood to eddy, the resulting hemodynamics may lead to increased clot formation in the region.

Additionally, the use of an artificial sinus only applies to patients that are receiving an aortic graft in addition to a replacement valve. An expandable aortic graft is not introduced into a patient who requires only valve replacement. Thus, the need has been felt for a prosthetic mechanical valve which mitigates potentially damaging shock forces in any patient that receives such an artificial valve.

SUMMARY OF THE INVENTION

In one aspect of the invention, a biocompatible valve is provided for implanting into a biological organism to confine flow of a biological fluid to a single direction. The valve includes a mount which is affixable to the organism. The mount has a first aperture and a second aperture formed in an opposing relationship for allowing the fluid to flow longitudinally through the mount. The valve also includes a valve mechanism which is operable into an open position or a closed position. The valve mechanism has an orifice formed therein, which is coaxially aligned with the first aperture and the second aperture of the mount. The valve mechanism is longitudinally displaceable in the mount between the first aperture and the second aperture. The valve further includes a dampening mechanism coupled to the mount and operable to dissipate the hydraulic shock energy at the orifice resulting from the interruption of fluid flow when the valve closes.

In another aspect of the invention, a biocompatible valve includes a mount fixable to the organism and operable to allow the fluid to flow along a longitudinal axis thereof. The valve includes a valve mechanism which is coaxially displaceable in the mount and operable into a closed or open position. The valve mechanism has a first and second aperture formed therein in opposing relationship for allowing the fluid to flow longitudinally through an orifice defined by those apertures. The valve further includes a dampening mechanism coupled to the mount and operable to dissipate hydraulic shock energy at the orifice resulting from an interruption of the fluid flow by a transition of the valve mechanism from the open position to the closed position. The dampening mechanism is coupled to the valve mechanism around an outer circumference thereof between the first and second apertures.

In yet another aspect of the invention, a biocompatible valve is provided for implanting into a biological organism so as to confine flow of a biological fluid to a single direction. This valve includes a mount affixable to the organism and operable to allow the fluid to flow along a longitudinal axis thereof. The valve also includes a valve mechanism coaxially displaceable in the mount and operable into an open and closed position. The valve mechanism has a first and second aperture formed in opposing relationship therein to allow the fluid to flow longitudinally through an orifice defined therebetween. The valve also includes a dampening mechanism coupled between the mount and the valve mechanism and responsive to at least one predetermined frequency component of a hydraulic shockwave at the orifice resulting from an interruption of fluid flow by a transition of the valve mechanism from the open to the closed position.

In still another aspect of the invention, a biocompatible valve is provided that includes a valve body affixable to the organism and operable to allow the fluid to flow along in a longitudinal axis thereof. The valve body has formed in opposing relationship thereon a first and second aperture for allowing the fluid to flow longitudinally through an orifice defined therebetween. The valve also includes a closing mechanism coupled to the valve body and positioned in the valve body and operable into one of a closed and open position. The closing mechanism has a closed surface on which at least a portion thereof is longitudinally displaceable in the valve body so as to dissipate hydraulic shock energy at the orifice resultant from an interruption of the fluid flow by a transition of the closing mechanism from the open to the closed position.

In yet another aspect of the invention, a biocompatible valve includes a mount affixable to the organism and operable to allow the fluid to flow along a longitudinal axis thereof. A valve mechanism is provided to be coaxially displaceable in the mount and operable to impart a first change of pressure to the fluid upon a mechanical transition thereof. A biasing mechanism is coupled to the valve mechanism and responsive to the first change of pressure. The biasing mechanism is operable in a first direction to decrease the first change of pressure and operable in a second direction to impart a second change of pressure to the fluid.

BRIEF DESCRIPTION OF THE DRAWINGS

FIGS. 1A-1B are illustrations of a replacement valve and expandable aortic graft of the prior art;

FIG. 8A is a cross-sectional view of another embodiment of the present invention;

FIG. 8B is an illustration of an exemplary pivot dampening mechanism introduced to the biocompatible valve of FIG. 8A;

FIG. 8C is a side view of the dampening mechanism and leaflet mount of the biocompatible valve of FIG. 8A;

DETAILED DESCRIPTION OF PREFERRED EMBODIMENTS

Various exemplary embodiments of the present invention will now be described in conjunction with the illustrations of the Drawings. It is to be understood that the Drawings are not scaled mechanical drawings, but are diagrams intended to show the combination of features which form the invention when embodied as depicted.

Figure 2A:
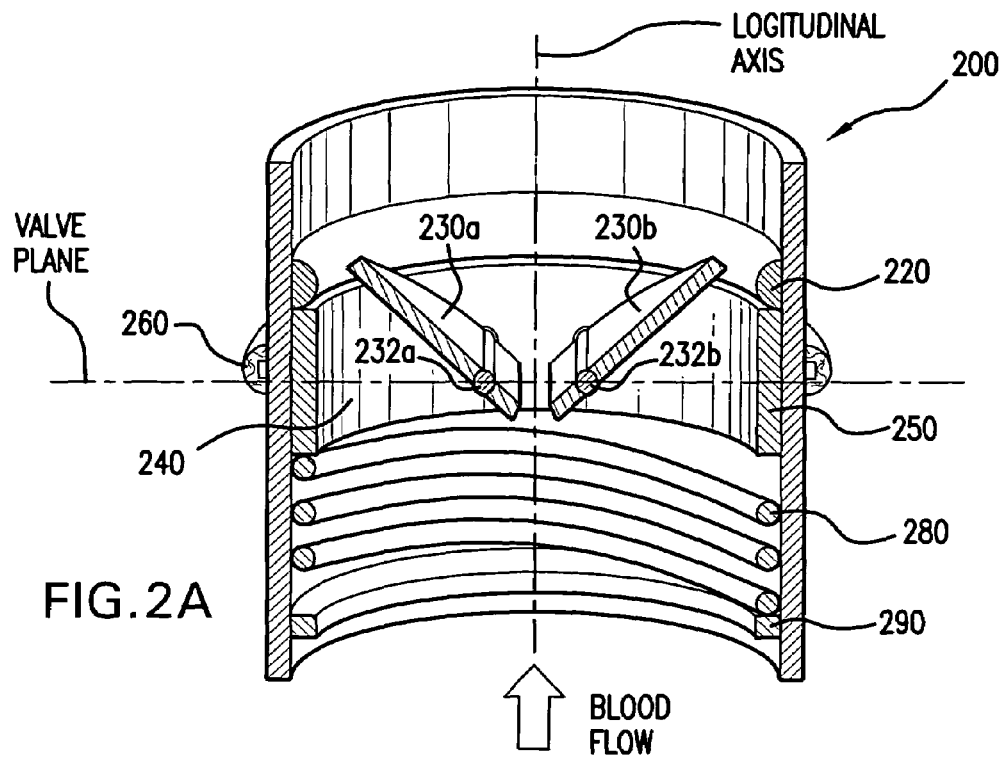
FIGS. 2A-2B are diagrams illustrating fundamental concepts of the invention.
Figure 2B:
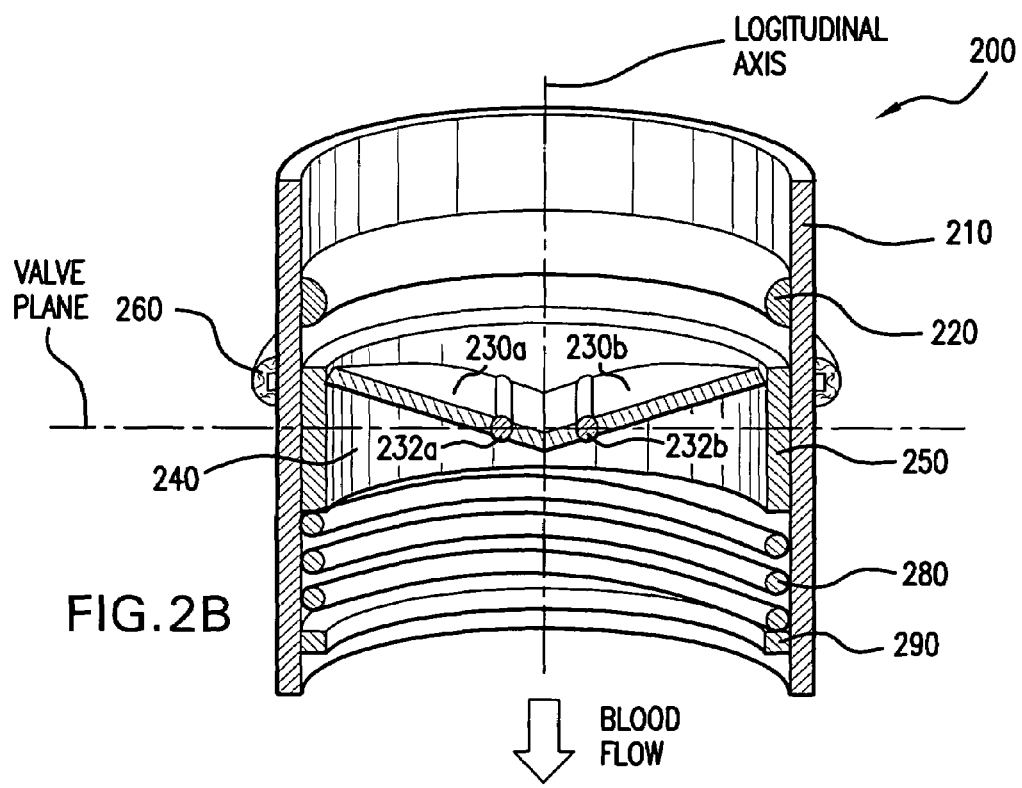

Referring to FIGS. 2A and 2B, there is shown in cross-section a biocompatible valve 200 operable in accordance with the invention. As is shown in the Figure, the valve 200 includes a mount 210 having a longitudinal axis along which blood flows. The mount 210 is affixable to the patient by affixing means, which may be any known means for affixing a replacement valve into a patient known in the art, such as by suture cuff 260. Additionally, the affixing means need not be located at the midpoint as shown in the Figure. In certain embodiments of the invention, the valve 200 will be formed into or make a part of an aortic graft in which case the suture cuff 260 or other attachment means may be located closer to the ends of the graft.

The valve 200 further includes a valve annulus 250, which is received in the mount 210 and is longitudinally displaceable therein. The valve annulus 250 defines a valve orifice 240 coaxially residing on the longitudinal axis of the mount 210. The valve orifice 240 has pivotally coupled thereto leaflets 230a, 230b by way of a corresponding leaflet pivot 232a, 232b. The leaflets 230a, 230b, embody the closing mechanism for the valve.

As is shown in the Figures, the valve 200 has a biasing mechanism 280, which is shown as a coiled spring. The coil spring may be made of any biocompatible material, such as titanium or pyrolytic carbon. However, a coiled spring may not provide the suitable biasing mechanism in every embodiment without some cover membrane such as Dacron®, Gortex® and/or anti-thrombolytic coating to prevent blood clots from forming interstitially to the coils of the spring. The biasing mechanism 280 shown as a coiled spring is illustrative of various aspects of the invention.

In certain embodiments of the invention, the valve annulus 250 is longitudinally displaceable against the biasing mechanism 280 so as to dissipate the hydraulic shock associated with the abrupt cessation of fluid motion when the valve leaves 230a, 230b undergo a transition from an open position to a closed position. In the embodiment of FIGS. 2A-2B, the biasing mechanism is unidirectional and as such, a valve displacement stop 220 is incorporated in the aperture of the mount 210 so as to limit the displacement of the valve annulus 250. The mount may further include at an opposing aperture thereof a biasing stop 290 against which the biasing mechanism 280 abuts.

Various operational features of the present invention will now be described with reference to FIGS. 2A-2B. FIG. 2A depicts the elements of the valve 200 during the systolic stage of a heartbeat cycle. Blood flow, as indicated by the arrow, flows away from the heart (hereinafter referred to as "downstream") and into the valve, thereby forcing the valve leaflets 230a, 230b into an open position. The biasing mechanism 280 applies a biasing force to the valve annulus 250 against the valve displacement stop 220 and is maintained in that position throughout the systolic stage. In the diastolic stage, as shown in FIG. 2B, the blood flow begins to reverse and at that point in time, the valve leaflets 230a, 230b close against the orifice 240 of the valve annulus 250. This mechanical transition of the valve's state abruptly stops the flow of blood resulting in fluid on the downstream side of the valve being compressed by its own momentum while the blood on the side of the valve leaflets 230a, 230b closest to the heart (hereinafter referred to as "upstream") rarefies. This establishes in the blood a shockwave characterized by a plurality of frequency components. In accordance with the invention, the pressure on the valve leaflets 230a, 230b is transmitted to the biasing mechanism 280 through the motion of the valve annulus 250 away from its stopped position, i.e., the position shown in FIG. 2A. The shockwave is then partially dissipated as thermal energy through a dampening mechanism and a portion of the associated energy may be returned to the fluid in a delayed fashion.

In certain embodiments of the invention, a characteristic spring constant of a biasing mechanism in combination with the mass of the valve mechanism, i.e., the mechanism of the valve annulus 250 and valve leaflets 230a, 230b combined, as well as the dynamics of the fluid and inter-element friction are adjusted to form a resonant dampener. As is well-known in the art, a simple damped system may be described by an equation such as:

$$m\ddot{x}+c\dot{x}+kx=f(t),$$

where m is the suspended mass, c is a damping factor often referred to as viscous damping, and k is a stiffness or linear spring constant. The driving force is represented in the equation as f(t) and is often modeled as a summation of sinusoidal oscillations. The variable x refers to displacement, $\dot{x}$ is then velocity and $\ddot{x}$ is acceleration. The constants m, c and k are typically positive and fixed.

In the simple case, the spring force is linearly dependent on displacement and damping is linearly dependent on velocity. Damping tends to dissipate energy and a critically damped system will tend to do so in exactly one cycle of the natural frequency of the system. Introducing damping into a system also changes its natural frequency and, moreover, lowers the amplitude of the response to forced oscillations and broadens the range of frequencies to which the system responds.

As is well-known in the art, multiple linear systems can be coupled together to create more complex dampening responses. For example, a spring or biasing mechanism having a light stiffness may be coupled to a spring with a larger degree of stiffness to produce higher-order frequency response mechanisms.

Higher-order or nonlinear terms may be introduced to the system equation given above. Generally speaking, one or more of the coefficients m, c, or k in the equation above may be dependent on displacement, velocity, or another parameter rather than being fixed. Exemplary non-linear systems include friction damping, which is not proportional to velocity, turbulent flow damping, which is proportional to the square of the velocity, asymmetric damping, where a response to a positive velocity differs from a response to a negative velocity, asymmetric spring stiffness, where a positive displacement is treated differently than a negative displacement, displacement dependent damping or spring stiffness, amplitude dependent damping or spring stiffness, velocity dependent damping or spring stiffness, frequency dependent damping or spring stiffness, and negative damping or spring stiffness. Such nonlinear damping may be implemented by embodiments of the present invention.

It should be noted that the system of the present invention may be strongly coupled to the surrounding circulatory system in an asymmetric fashion. Forward blood flows open the valve, minimizes resistance to fluid flow and likewise minimizes resistance to the displacement of the valve plane through the fluid. Reverse flow closes the valve and maximizes resistance to fluid flow and likewise maximizes resistance to valve plane displacement. In the closed state, the valve plane will more easily be displaced upstream than downstream because of the asymmetric operation of the valve flaps. For example, in the case of an aortic heart valve, when the valve is closed and under load from the aorta, the mass of the valve will be coupled to the mass of the fluid, arterial blood pressure will assert positive displacement force on the valve plane, and the fluid will provide coupling between the valve plane and elastic body tissues. Meanwhile, upstream of the valve, low pressure conditions will produce different or complementary coupling and decoupling relationships.

In a tuned damped valve system implemented in accordance with the present invention, effective spring force, damping and mass are all subject to complex and dynamic relationships that vary over the cardiac cycle. For the present invention, where the goal is to mitigate shock and resonance from the valve closure, the system will be preferentially tuned to respond with proper damping characteristics during the period of loading by the valve being closed and during the transition to valve leaflet closure. Operating characteristics during other phases of the cardiac cycle may then be considered in order to fine tune the system and in particular, to insure that the basic function of the valve is not compromised.

Tuned damping can also introduce a phase-lag in the motion of the valve plane that helps cancel out reflections of the shockwave from downstream tissues. Moreover, the combination of rapid absorption of a shock by downstream displacement of the valve plane and the subsequent release of energy more slowly back into the downstream chamber through damped return of the valve plane can be adjusted to provide more uniform blood pressure and blood flow over the cardiac cycle, providing some of the advantages described above with regard to the artificial sinuses of the prior art, but with less susceptibility to performance degradation from fibrous scaring.

The return of the valve plane to a predetermined position may also be adjusted to either lead or lag the mean heart rate in order to increase performance. The mean displacement position of the valve-plane may change with increasing heart rate, and certain embodiments of the invention employ progressive biasing or damping to adapt the system response to the heart rate.

By introducing proper damping, the suspension system can be tuned to return energy gently to the fluid so that blood pressure is maintained, but resonant waves in the fluid are canceled. Leaflet impact may also be cushioned by tuning the dampening mechanism to react in accordance with leaflet closure timing. Moreover, a slow release of absorbed displacement energy back to the blood stream on the same time scale as mean heart rate will help to maintain uniform blood pressure and blood flow over the cardiac cycle in a fashion similar to natural action of the elastic arterial vessel walls. Asymmetric biasing or damping of the biasing elements of the system can be used to optimize the return of energy, while minimizing stress on both the valve and on biological tissues.

The suspension system of the present invention does not significantly reduce the efficiency of blood pumping by the heart and may ensure such by minimizing the mean upstream motion of the valve leaflets after closure. When the biasing force is adjusted so that it is sufficient to balance mean downstream blood pressure in the closed position, transient over-pressure from incident shock energy will be reduced, but net backflow will be prevented.

Figure 3:
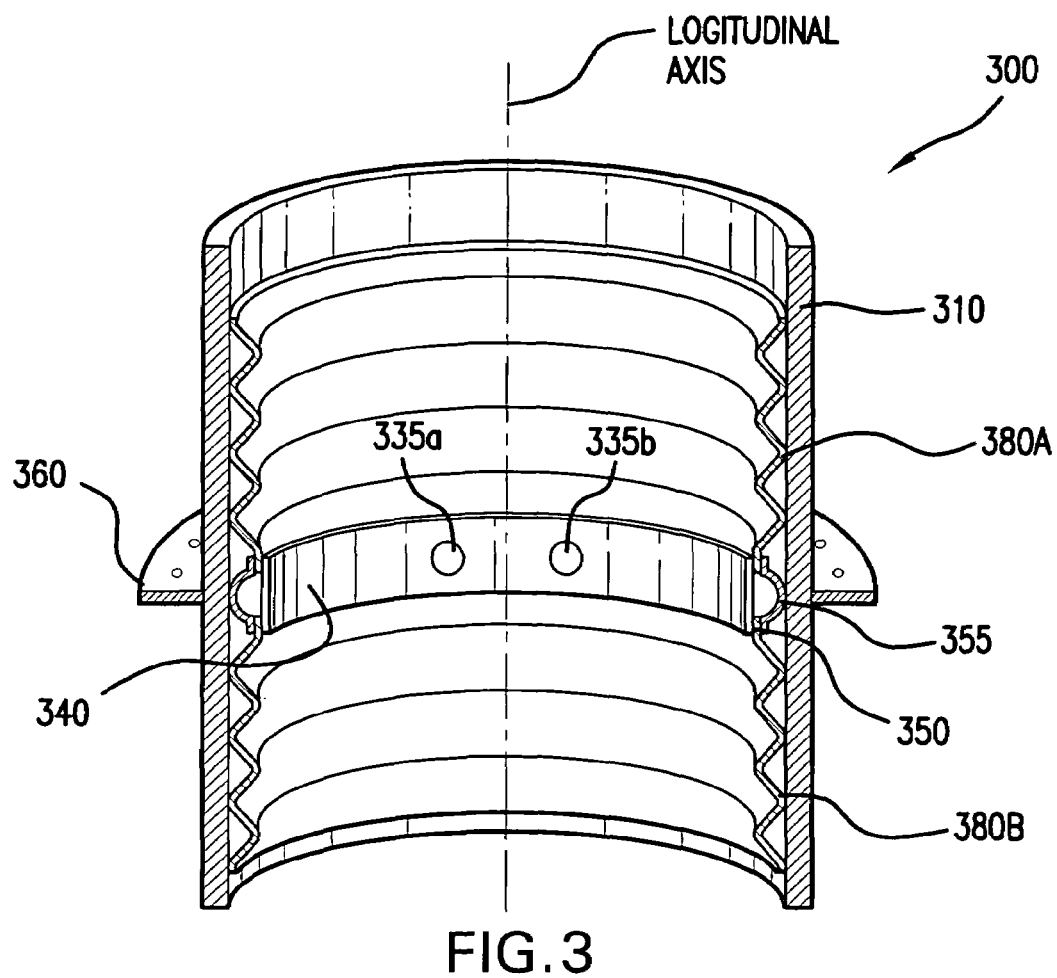
FIG. 3 is a cross-sectional view of one embodiment of the present invention.

FIG. 3 is a cross-sectional diagram of another exemplary embodiment of the present invention. The valve 300 includes a mount 310 for affixing to a patient by affixing means, such as the suture ring 360. Coaxially aligned with the mount and positioned therein is the valve annulus 350, which is longitudinally displaceable in the mount 310. The valve annulus 350 may have appropriate guide means 355 to properly space the valve annulus 350 from the mount 310 and to afford the valve annulus 350 easy longitudinal movement therein. The valve annulus 350 defines the valve orifice 340 in which the valve leaflets (not shown) are received through the pivot mounts 335*a*, 335*b*.

The valve annulus 350 is coupled to the mount 310 through biasing mechanism 380*a*, 380*b*. Under no load conditions, the valve annulus 350 is biased in a null position, such as that shown. The valve annulus 350 is then longitudinally displaced against the biasing mechanism 380*a*, 380*b* in both directions along the longitudinal axis of the valve 300. The exemplary embodiment of FIG. 3 can readily dissipate shock-wave energy that is periodic within the blood. That is to say, when compression appears on one side of the valve annulus and rarefaction of the blood occurs on the opposite side, the valve annulus 350 is forced in the direction corresponding to the compression. In periodic waves, where the compressed portion of the wave is followed by a region of rarefaction and followed by another region of compression, the valve annulus 350 moves within the mount 310 accordingly and provides a dampening force until the wave has been dissipated.

The mount 310 need not be rigid material, but may be a flexible material such as Dacron®, which forms the walls of a known prosthetic grafts. The Dacron® sheath functions primarily to prevent scar tissue from inhibiting the action of the bias mechanism. The mount 310 will preferentially be stiffer than the biasing mechanism 380*a*, 380*b* in the longitudinal direction in order to maintain proper action.

Biasing mechanism 380a, 380b is illustrated in FIG. 3 as crenulated tubes of a biocompatible semi-rigid material, such as a biocompatible polymer known in the art. The material may be chosen according to the amount of stiffness desired in the biasing mechanism 380a, 380b. Furthermore, as indicated above, biasing mechanism section 380a may be chosen to have a different stiffness than that of biasing mechanism section 380b. This allows the system to be tuned to a range of frequencies anticipated by a shockwave developed when the valve closes. Additional damping may be introduced by controlling friction between the biasing mechanism 380a, 380b or the guide 355 and the mount 310, or by other means discussed herein.

Biasing mechanism 380a, 380b is coupled to the mount at corresponding apertures thereof by means known in the art, such as by suture, by thermal fusion, or by a biocompatible adhesive. The same means for coupling to the mount may be used to affix the biasing mechanism to the valve annulus 350.

Figure 4:
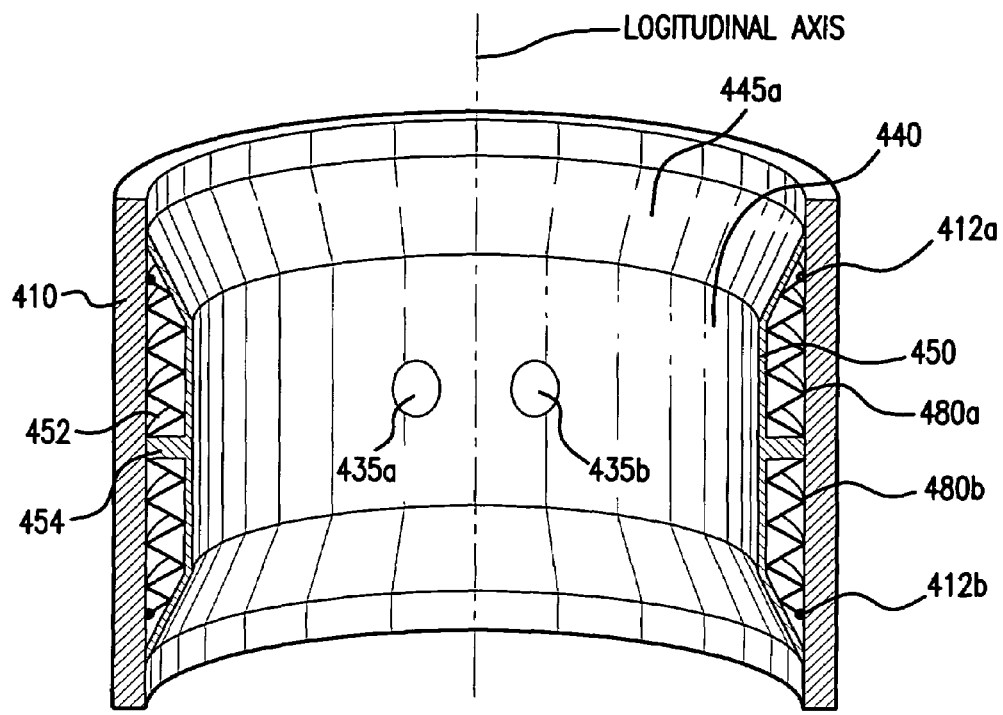
FIG. 4 is a cross-sectional view of another embodiment of the present invention.

Referring now to FIG. 4, there is shown another embodiment of the present invention by which displacement of the valve annulus is allowed in two directions. As is shown in the Figure, the valve annulus 450 is longitudinally displaceable in the mount 410 and has formed around its circumference a chamber 452 for receiving therein the biasing mechanism 480a, 480b. The valve annulus 450 has formed thereon an orifice 440 which includes sloped transition sections 445a, 445b. The transition sections 445a, 445b promote smooth flow of blood through the orifice 440 while offering minimal resistance thereto. The valve orifice 440 also has formed thereon pivot mounts 435a, 435b into which the valve leaflets (not shown) are received.

In certain embodiments of the present invention, the circumferential chamber 452 will have formed therein a circumferential compression tab 454 for coupling the biasing mechanism 480a, 480b to the valve annulus 450. Within the chamber, the biasing mechanism 480a, 480b are coupled to the mount at 412a, 412b, respectively, by means known in the art such as by thermal fusion or by an adhesive. Alternatively, the coupling at 412a, 412b may be achieved by forming an appropriate circumferential biasing stop to abut with the corresponding biasing section 480a, 480b.

The exemplary embodiment illustrated in FIG. 4 may be further configured with biasing mechanism sections 480a, 480b of different characteristic stiffness for purposes of resonant damping. The biasing mechanism sections 480a, 480b may be formed from a crenulated tube of suitable material, a material having a predetermined compressible or tensile elasticity, a coil spring, or any other biasing means known in the art. Damping may be tuned by material properties, friction and fluid dynamics.

Figure 5:
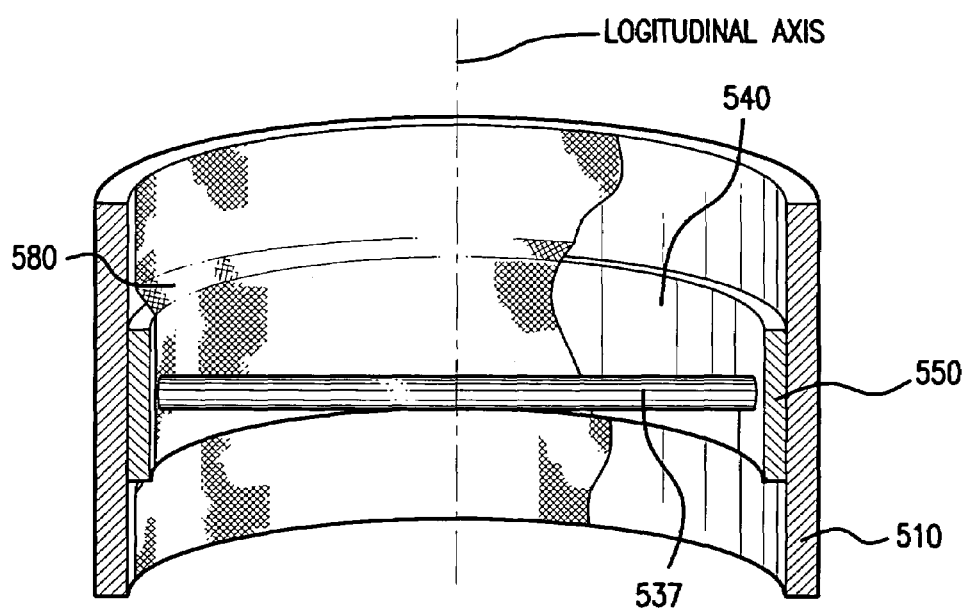
FIG. 5 is a cross-sectional view of another embodiment of the present invention.
Figure 6:
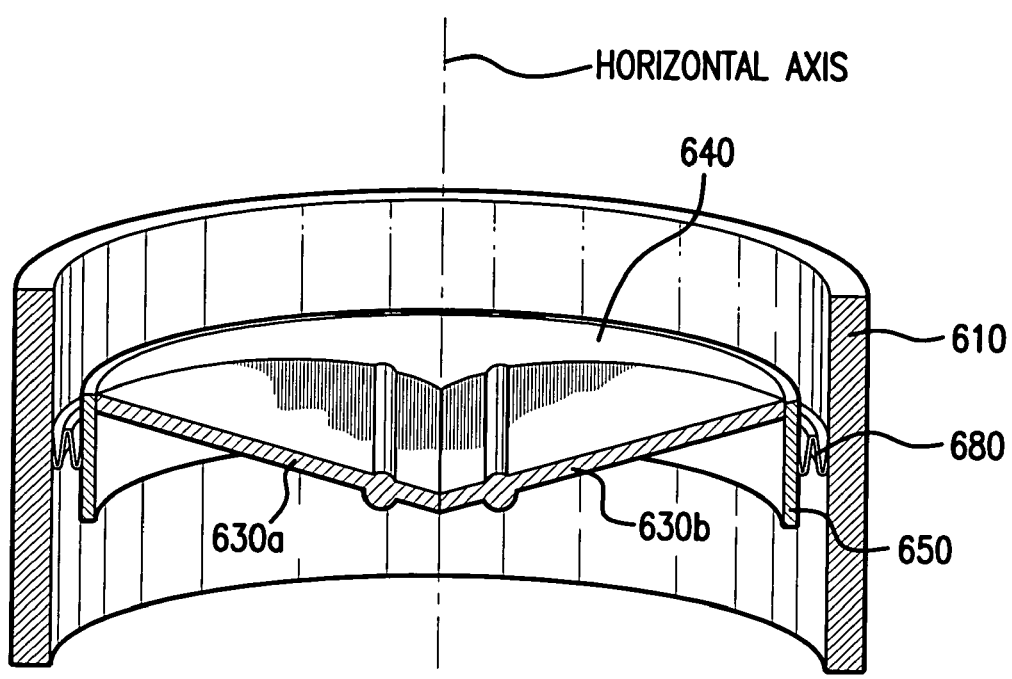
FIG. 6 is a cross-sectional view of another embodiment of the present invention.

Another exemplary embodiment of the present invention is illustrated in FIG. 5, where the biasing mechanism 580 is formed of a biocompatible elastic band coupled to the mount 510. The valve annulus 550 is displaceable longitudinally within the mount 510 and is biased to a null position by biasing mechanism 580. The biasing means may be fused or otherwise adhered to the inner peripheral walls of the mount 510 and may allow the valve annulus 550 to move freely beneath the band 580. The band 580 may include openings formed therein to allow the insertion of a pivot rod 537 on which the leaflets are mounted. The band 580 can be chosen to have the appropriate elasticity to correspond to the expected blood pressure and frequency components of the shockwave energy, and damping can be modified by friction and flow characteristics An alternative embodiment of the present invention is exemplified in the diagram of FIG. 6. As is shown in the Figure, the valve annulus 650 is suspended in the mount 610 by a circumferential biasing mechanism 680. The biasing mechanism 680 may be formed in a bellows fashion from a material appropriate to the desired stiffness. The valve annulus 650 is adapted to pivotally receive the valve leaflets 630a, 630b.

In other embodiments of the invention, the suspended valve annulus 650 and the biasing mechanism 680 are tuned to a resonant frequency of the shock wave, as previously discussed. Additionally, the motion of valve annulus 650 and the biasing mechanism 680 may be sized in both physical dimension and in mass to promote continual blood surges in the region as the annulus moves so as to wash the area between the mount 610 and the valve annulus 650. The displacement of blood from this region may be used in certain embodiments of the invention as an additional, tunable damping parameter of fluid resistance.

Additionally, the material forming the biasing mechanism 680 may be of a material, or may have a specific profile, or may be a composite material, or may be a layered laminated material to allow different characteristics of motion in one direction than in the opposing direction. These characteristics may be adjusted, as is known in the art, to achieve the desired response to the shock energy.

Figure 7A:
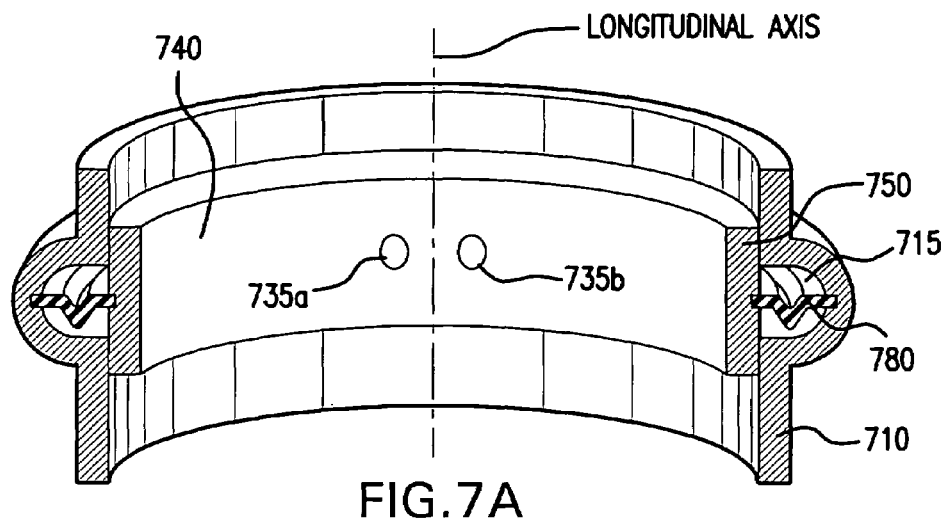
FIGS. 7A-7C are cross-sectional views of another embodiment of the present invention.
Figure 7B:
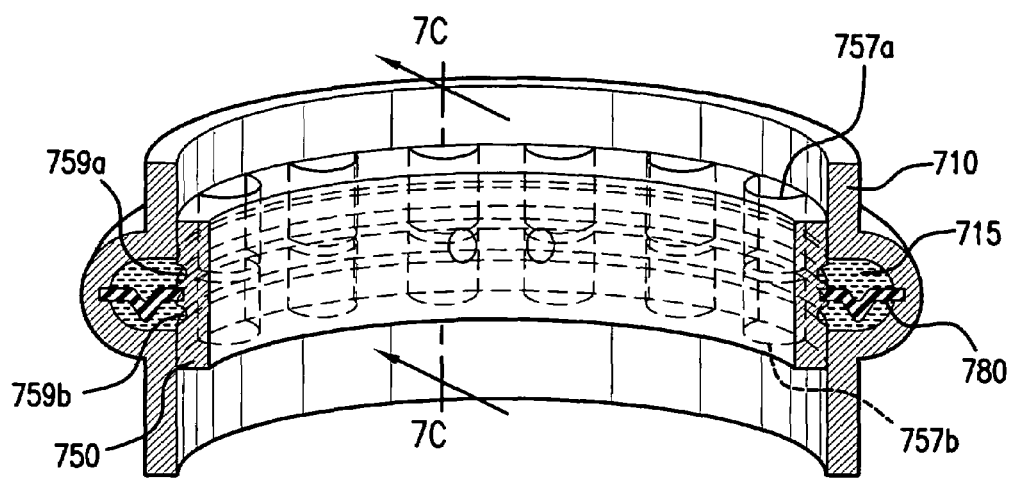
Figure 7C:
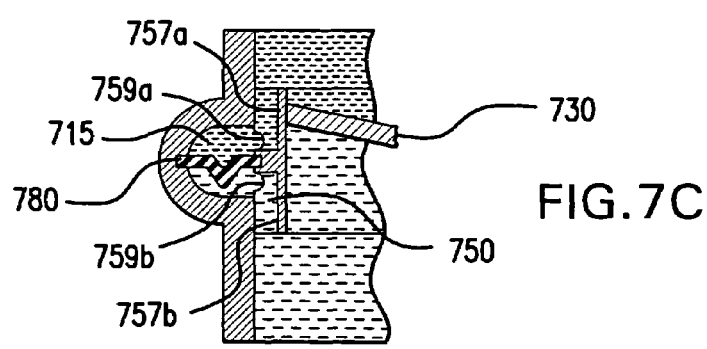

In another embodiment of the present invention, and as exemplified in FIGS. 7A-7C, the mount 710 has formed therein a circumferential channel 715 into which the biasing mechanism 780 is received. This embodiment allows the valve orifice 740 to be of a larger diameter than in embodiments previously described. The orifice 740 in the valve annulus 750 receives the closing mechanism, such as the leaflets previously described, in mounting holes 735a, 735b.

In the embodiment shown in FIG. 7a, the circumferential chamber 715 may be filled with a material to respond in conjunction with that of biasing annulus 780. The addition of a second biasing material into the biasing mechanism, together with inter-surface friction, may be used to tune the response of the valve to a range of frequencies expected in the shockwave energy.

Alternatively, blood may be introduced to the circumferential chamber 715 to both wash the biasing mechanism and to provide a tunable fluid damping action. The circumferential chamber 715 may be sized to receive a certain amount of fluid via longitudinal channels 757a, 757b formed in the valve annulus 750. The longitudinal channels 757a, 757b may be coupled with other such channels via a corresponding one of a pair of circumferential channels 759a, 759b. The size and fluid flow characteristics of the circumferential channels 759a, 759b, the size and fluid flow characteristics of the longitudinal channels 757a, 757b may be adjusted to tune the response to hydraulic shock. Moreover, the pairs of longitudinal channels 757a, 757b may include channels of different radii to provide longitudinal movement of valve annulus 750 preferentially in one direction over another. As is shown in FIG. 7c, the chamber 715, the biasing annulus 780 and the opposing channels 757a, 757b are structured to prevent blood from leaking across the valve closure plane, i.e., the two sides are isolated when the valve leaflets 730 are closed.

Aspects of the invention may be achieved by allowing the closure plane of the closure mechanism to move longitudinally with respect to the mount. For example, as is shown in FIGS. 8A-8B, the leaflet 830 is received in the leaflet mount 835 on opposing sides of the mount 810 in the orifice 813. The leaflet mount 835 may be filled with a compressible elastic material 880a and then held in place from the outer surface of the mount 810 by a suitable cover plate or plug 812. The inner side of the leaflet mount 835 may be covered by a flexible membrane 814 to allow the leaflet pivot 837 to move longitudinally within the receiving port 835 but to prevent fluid from collecting therein.

As is shown in FIG. 8C, the leaflet mount 835 may receive biasing material 880a, 880b to provide damping in two directions. The damping mechanism may also be formed from a coil spring, leaf spring, or other like spring mechanism. As previously stated, any of the materials and/or structures used in the biasing mechanism may be asymmetrically distributed in the leaflet mount 835 to provide tuning to the valve system, as previously described. Additionally, in certain embodiments of the invention, the leaflet mount structure exemplified in FIGS. 8A-8C may be incorporated into the valve annulus of other embodiments, such as those previously described, so as to produce a higher order response mechanism to the shock energy.

Figure 9A:
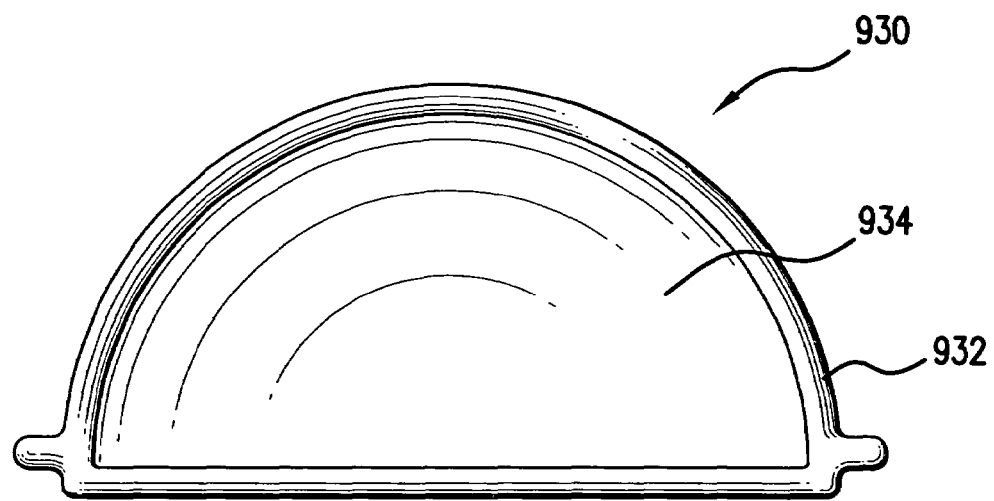
FIGS. 9A-9B are illustrations of a flexible leaflet for use in certain embodiments of the present invention; and, FIG. 10 is a cross-sectional view of another embodiment of the present invention.
Figure 9B:
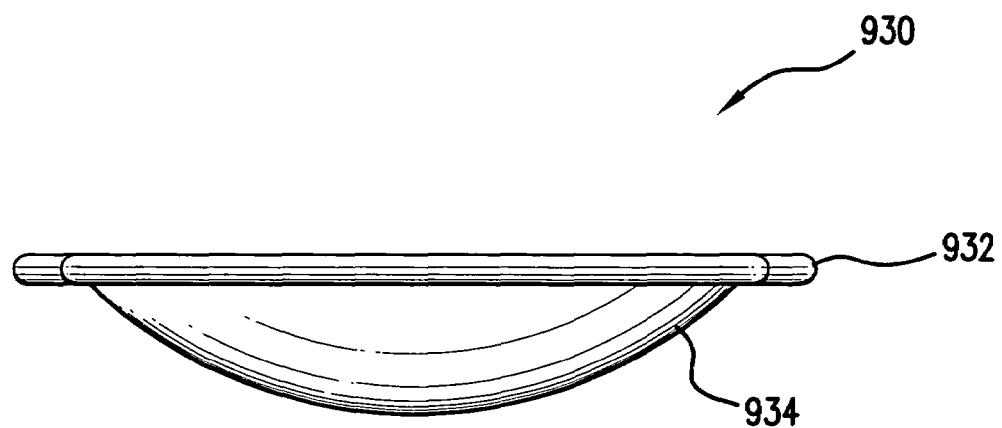

The valve closure plane may also be moved by means of a deformable leaflet, as shown in FIG. 9A-9B. The leaflet 930 may be composed from an elastic material of predetermined stiffness mounted on a rigid frame 932. The deformable portion 934 then provides the desired response to the shockwave energy. The deformable leaflet 930 may be used in conjunction with any of the biasing mechanisms previously described to produce higher order responses to the shockwave.

Figure 10:
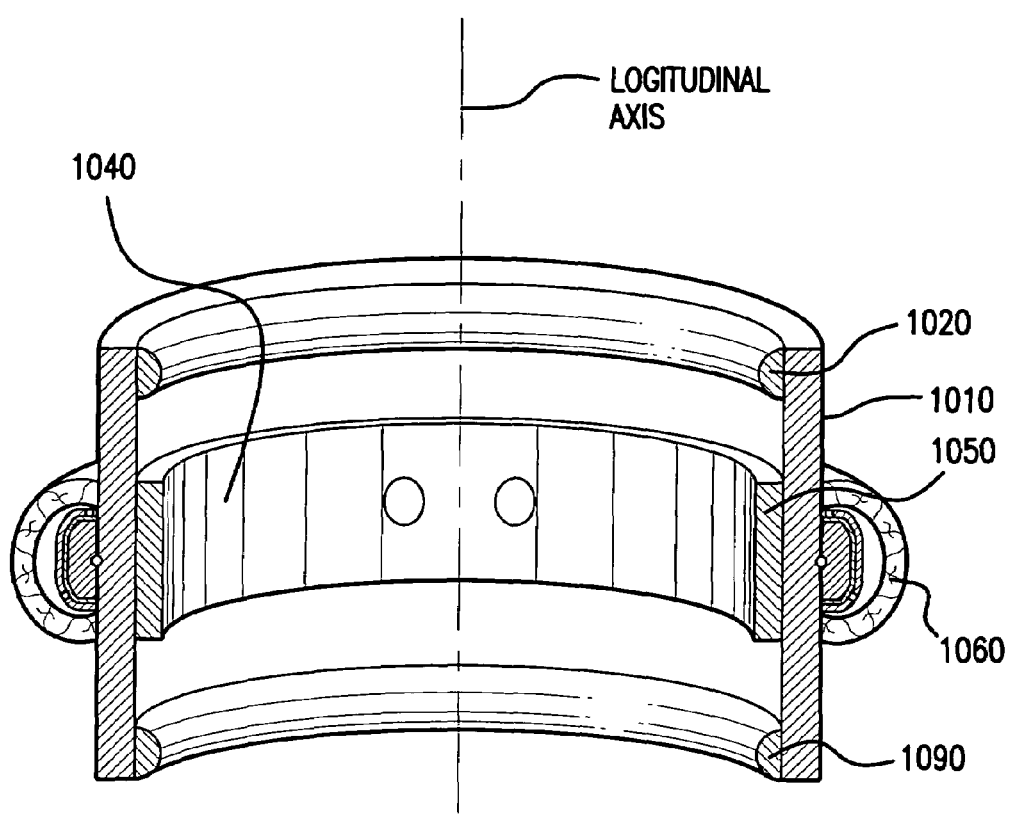

Referring now to FIG. 10, there is shown an alternative embodiment of the present invention in which the valve annulus 1050 is free to move within the mount 1010 to the limit of the stops 1020, 1090. No spring or restorative force is used as the biasing; only the gradients in the blood pressure flow. Dampening is provided by friction between the walls of the mount 1010 and the valve annulus 1050. The friction is coupled with the fluid dynamics of the flowing blood to provide the necessary longitudinal movement in response to the shock energy.

During the forward blood flow, the gradient across the valve orifice 1040 will induce movement into the valve body 1050 as the valve leaflets (not shown) open. As blood flow reverses, the leaflets will begin to close and, at the same time, the valve annulus 1050 will tend towards a neutral position. A damping on the sliding action of the valve annulus 1050 may be adjusted so that the leaflets will strike the valve orifice 1040 while the valve body 1050 is in motion, thereby cushioning the impact since the relative closing speed of the leaflet to orifice rim is reduced. If the valve annulus 1050 is then slowed gradually with appropriate damping force, an abrupt shock will be avoided in that the energy will be distributed over a broader time period. Furthermore, any resident longitudinal pressure waves induced beyond the heart valve by the closure thereof that are reflected back to the valve orifice 1040 will tend to displace orifice 1040 by a damped motion, further dissipating energy. The system can be adjusted so that the leaflet closure and displacement correction are timed appropriately under operating conditions. Resonance of the system can be tuned for most effective damping by controlling the mass of the structure and its dynamic fluid coupling No specific spring force is present in this embodiment. Restorative force is provided by blood flow pressure gradients. Damping may be provided by various means, such as varying the friction between the mount 1010 and the valve annulus 1050 and by adjusting the mass of the valve annulus and leaflets. The friction may be adjusted by means of a materials choice, texturing or by a gradual sloping of the mount walls. Damping may be fixed throughout the range of motion or may be induced progressively. Damping may be increased at approximately the point at which normal leaflet impact would occur so as to slow the travel and absorb the shock energy smoothly. Damping may also be made directionally asymmetric through the use of microwedge texturing of the inner wall of the mount and the outer wall of the valve annulus 1050. Hemodynamics may be utilized to provide damping through fluid flow resistance by shaping of the surfaces over which the blood flows, including the leaflets, inner surface of the mount, outer surface of the valve annulus and stop rings. The travel of the valve annulus 1050 over the inner surface of the mount 1010 washes the walls of the mount on each stroke thereby reducing thrombolitic events and infection. However, typically the inner face edges of the valve annulus 1050 and the stop rings 1090, 1020 will be smooth to minimize any negative hemodynamic effects.

The descriptions above are intended to illustrate possible implementations of the present invention and are not restrictive. Many variations, modifications and alternatives will become apparent to the skilled artisan upon review of this disclosure. For example, components equivalent to those shown and described may be substituted therefore, elements individually described may be combined, and element described as discrete may be distributed across many components. The scope of the invention should therefore be determined not with reference to the description above, but with reference to the appended claims, along with their full range of equivalence.

What is claimed is:

1. A biocompatible valve for implanting in a biological organism to confine flow of a biological fluid to a single direction, the valve comprising:
   a mount affixable to the organism, said mount having a first aperture and a second aperture formed in opposing relationship therein for allowing the fluid to flow longitudinally through said mount;
   a valve mechanism operable into one of an open position and a closed position, said valve mechanism having formed therein an orifice coaxially aligned with said first aperture and said second aperture of said mount, said valve mechanism including a supporting portion for supporting at least one leaf member in pivotally displaceable manner relative thereto, said supporting portion being longitudinally displaceable in said mount between said first aperture and said second aperture; and
   a dampening mechanism element coupled to said valve mechanism and said mount, said dampening mechanism displaceably maintaining said supporting portion of said valve mechanism for displacement within said mount subsequent to leaf member closure, said dampening mechanism being operable to dissipate energy at said orifice transferred to said valve mechanism by a mechanical transition thereof.

2. The biocompatible valve as recited in claim 1, wherein said mount includes at least one stop operable to limit thereat said longitudinal displacement of said valve mechanism, said dampening mechanism including a biasing element operable to said valve mechanism against said stop when in said open position.

3. The biocompatible valve as recited in claim 1, where said dampening mechanism includes a first biasing element and a second biasing element.

4. The biocompatible valve as recited in claim 3, wherein said first biasing element and said second biasing element are respectively coupled to said mount at said first aperture and said second aperture thereof.

5. The biocompatible valve as recited in claim 3, wherein said first biasing element and said second biasing have a corresponding biasing characteristic each distinct from the other.

6. The biocompatible valve as recited in claim 5, wherein said biasing characteristic is a spring constant.

7. The biocompatible valve as recited in claim 1, wherein said dampening mechanism is responsive to at least one predetermined frequency component of a hydraulic shock wave associated with said energy.

8. A biocompatible valve for implanting in a biological organism so as to confine flow of a biological fluid to a single direction, the valve comprising:
a mount affixable to the organism and operable to allow the fluid to flow along a longitudinal axis thereof;
a valve mechanism including a supporting portion for supporting at least one leaf member in pivotally displaceable manner relative thereto, said supporting portion being coaxially displaceable in said mount and operable into one of an open position and a closed position, said valve mechanism having formed in opposing relationship thereon a first aperture and a second aperture for allowing the fluid to flow longitudinally through an orifice defined therebetween; and
a dampening mechanism element coupled to said valve mechanism and said mount, said dampening mechanism displaceably maintaining said supporting portion of said valve mechanism for displacement within said mount subsequent to leaf member closure, said dampening mechanism being operable to dissipate energy at said orifice imparted to the fluid resultant from a mechanical transition of said valve mechanism, said dampening mechanism coupled to said valve mechanism around an outer circumference thereof between said first aperture and said second aperture.

9. The biocompatible valve as recited in claim 8, wherein said dampening mechanism is an annular ring of an elastic material.

10. The biocompatible valve as recited in claim 8, wherein said dampening mechanism is a crenulated annulus of a semi-rigid material.

11. The biocompatible valve as recited in claim 8, wherein said mount includes a recess circumferentially disposed thereon, said dampening mechanism contained in said recess.

12. The biocompatible valve as recited in claim 8, wherein said dampening mechanism is responsive to at least one predetermined frequency component of a hydraulic shock wave associated with said energy.

13. A biocompatible valve for implanting in a biological organism so as to confine flow of a biological fluid to a single direction, the valve comprising:
a mount affixable to the organism and operable to allow the fluid to flow along a longitudinal axis thereof;
a valve mechanism including a supporting portion for supporting at least one leaf member in pivotally displaceable manner relative thereto, said supporting portion being coaxially displaceable in said mount and operable into one of an open position and a closed position, said valve mechanism having formed in opposing relationship thereon a first aperture and a second aperture for allowing the fluid to flow longitudinally through an orifice defined therebetween; and
a dampening mechanism element coupled to said valve mechanism and said mount, said dampening mechanism displaceably maintaining said supporting portion of said valve mechanism for displacement within said mount subsequent to leaf member closure, said dampening mechanism being responsive to at least one predetermined frequency component of a hydraulic shock wave at said orifice resultant from interruption of the fluid flow by a transition of said valve mechanism from said open position to said closed position.

14. The biocompatible valve as recited in claim 13, wherein said dampening mechanism is responsive to a predetermined band of frequencies.

15. The biocompatible valve as recited in claim 14, wherein said dampening mechanism is unresponsive to at least one frequency associated with said fluid flow.

16. A biocompatible valve for implanting in a biological organism so as to confine flow of a biological fluid to a single direction, the valve comprising:
a valve body affixable to the organism and operable to allow the fluid to flow along a longitudinal axis thereof, said valve body having formed in opposing relationship thereon a first aperture and a second aperture for allowing the fluid to flow longitudinally through an orifice defined therebetween; and
a closing mechanism coupled to said valve body and positioned in said valve body, said closing mechanism operable into one of a closed position and an open position, said closing mechanism including a supporting portion for supporting at least one leaf member in pivotally displaceable manner relative thereto, said closing mechanism including a dampener operably coupled to said supporting portion and said valve body, said dampener element maintaining said supporting portion to be longitudinally displaceable in biased manner within said valve body subsequent to leaf member closure, so as to dissipate hydraulic shock energy at said orifice resultant from interruption of the fluid flow by a transition of said closing mechanism from said open position to said closed position.

17. The biocompatible valve as recited in claim 16, wherein said closing mechanism includes at least one valve leaf pivotally received in openings formed in said orifice of said valve body, said valve leaf being formed of a deformable material.

18. The biocompatible valve as recited in claim 17, wherein said deformable material is responsive to at least one predetermined frequency of a hydraulic shock wave associated with said shock energy.

19. The biocompatible valve as recited in claim 17, wherein said closing mechanism includes at least one valve leaf pivotally received in openings formed in said orifice of said valve body, said openings each containing a biasing element for biasing said valve leaf.

20. The biocompatible valve as recited in claim 19, wherein said biasing element is responsive to at least one predetermined frequency of a hydraulic shock wave associated with said shock energy.

21. The biocompatible valve as recited in claim 16, further including a dampening mechanism coupled between said valve body and said mount.

22. The biocompatible valve as recited in claim 21, wherein said dampening mechanism is responsive to at least one predetermined frequency of a hydraulic shock wave associated with said shock energy.

23. A biocompatible valve for implanting to a biological organism so as to confine flow of a biological fluid to a single direction, the valve comprising:
a mount affixable to the organism and operable to allow the fluid to flow along a longitudinal axis thereof;
a valve mechanism including a supporting portion for supporting at least one leaf member in pivotally displaceable manner relative thereto, said supporting portion being coaxially displaceable in said mount and operable to impart a first change of pressure to the fluid upon a mechanical transition thereof; and a biasing mechanism element coupled to said valve mechanism and said mount, said biasing mechanism displaceably maintaining said supporting portion of said valve mechanism for displacement within said mount subsequent to leaf member closure, said biasing mechanism being responsive to said first change of pressure, said biasing mechanism operable in a first direction to decrease said first change of pressure and operable in a second direction to impart a second change of pressure to the fluid.

24. The biocompatible valve as recited in claim 23, wherein a characteristic of said biasing mechanism predetermined to return pressure of the fluid to a nominal value by said second change of pressure.

25. The biocompatible valve as recited in claim 23, wherein said second change of pressure occurs over a longer period of time than said first change in pressure.

26. The biocompatible mount as recited in claim 3, wherein said valve mechanism has formed between said first aperture and said second aperture thereof a circumferential chamber having a circumferential compression tab formed at substantially at a middle portion thereof, said first biasing element and said second biasing element respective coupled to said mount at one end thereof and said compression tab at an opposing end thereof.

27. The biocompatible mount as recited in claim 3, wherein said valve mechanism has formed between said first aperture and said second aperture thereof a circumferential chamber, said mount having formed thereon a circumferential compression tab received in said chamber of said valve mechanism, said first biasing element and said second biasing element respective coupled to said valve mechanism at one end thereof and said compression tab at an opposing end thereof.

28. The biocompatible valve as recited in claim 11, wherein said closure has a plurality of longitudinal channels formed in opposing pairs on an outer periphery of said valve mechanism, each channel of said pair having an open end at a corresponding aperture of said valve mechanism and a closed end at a mid-portion of said outer periphery of said valve mechanism, said closed end of each channel of said pair being on opposite sides of said dampening mechanism.

* * * * *